(12) United States Patent
Rührnschopf

(10) Patent No.: US 7,751,525 B2
(45) Date of Patent: Jul. 6, 2010

(54) METHOD FOR CORRECTING X-RAY SCATTER IN PROJECTION RADIOGRAPHY AND COMPUTER TOMOGRAPHY

(75) Inventor: Ernst-Peter Rührnschopf, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 321 days.

(21) Appl. No.: 11/903,145

(22) Filed: Sep. 20, 2007

(65) Prior Publication Data

US 2008/0075347 A1    Mar. 27, 2008

(30) Foreign Application Priority Data

Sep. 27, 2006    (DE)  ....................... 10 2006 045 722

(51) Int. Cl.
     *A61B 6/00*    (2006.01)
(52) U.S. Cl. ............................................. 378/7; 378/86
(58) Field of Classification Search ..................... 378/4, 378/5, 7
See application file for complete search history.

(56) References Cited

U.S. PATENT DOCUMENTS

| | | | | |
|---|---|---|---|---|
| 4,887,285 | A * | 12/1989 | Harding et al. | 378/88 |
| 4,918,713 | A * | 4/1990 | Honda | 378/98.4 |
| 5,315,506 | A * | 5/1994 | Wang et al. | 378/7 |
| 5,615,279 | A * | 3/1997 | Yoshioka et al. | 382/131 |
| 5,666,391 | A | 9/1997 | Ohnesorge et al. | |
| 5,878,108 | A * | 3/1999 | Baba et al. | 378/98.4 |
| 6,175,117 | B1 * | 1/2001 | Komardin et al. | 250/363.06 |
| 6,639,964 | B2 * | 10/2003 | Schneider et al. | 378/7 |
| 7,569,827 | B2 * | 8/2009 | Bai et al. | 250/363.04 |
| 2004/0202360 | A1 * | 10/2004 | Besson | 382/131 |
| 2004/0264629 | A1 * | 12/2004 | Tang | 378/7 |
| 2006/0008046 | A1 * | 1/2006 | Ruhrnschopf | 378/7 |

OTHER PUBLICATIONS

King et al., A Dual-Photopeak Window Method for Scatter Correction, The Journal of Nuclear Medicine, vol. 33, No. 4, Apr. 1992, pp. 605-612.*

Kyriakou et al., Combining deterministic and Monte Carlo calculations for fast estimation of scatter intensities in CT, Phys Med Biol, 51, 2006, pp. 4567-4586.*

Ohnesorge et al., Efficient object scatter correction algorithm for third and fourth generation CT scanners, Eur Radiol, 9, 1999, pp. 563-569.*

Zelleroff et al., Low contrast 3D-reconstruction from C-arm data, Medical Imaging, Proceedings of SPIE, vol. 5745, 2005, pp. 646-655.*

Love et al., Scatter estimation for a digital radiographic system using convolution filtering, Med Phys, 14, 2, Mar./Apr. 1987, pp. 178-185.*

(Continued)

*Primary Examiner*—Edward J Glick
*Assistant Examiner*—Alexander H Taningco

(57) ABSTRACT

The invention relates to a method for correcting x-ray scatter in projection radiography or in x-ray computer tomography, in which, for different observed objects, different scatter-correction convolution cores G are determined and in the examination of the respective objects object-specific scatter-correction convolution cores are applied to detector data which is created during the x-raying of these objects. The invention also relates to a projection radiography or x-ray computer tomography system which features programs in a processing system which executes the method described above when the system is operating.

18 Claims, 1 Drawing Sheet

OTHER PUBLICATIONS

Rinkel et al., Evaluation of a Physical Based Approach of Scattered Radiation Correction in Cone Beam CT for Non-Destructive Testing Applications, ECNDT, 2006, poster 39, pp. 1-11.*

Richard J. Warp, James T. Dobbins III; "Quantitative evaluation of noise reduction strategies in dual-energy imaging"; Med. Phys. 30 (2); Feb. 2003; pp. 190-198.

L. Alan Love and Robert A. Kruger; "Scatter estimation for a digital radiographic system using convolution filtering"; Med. Physics 14 (2), Mar./Apr. 1987; pp. 178-185.

J.A. Seibert, J.M. Boone; "X-ray scatter removal by deconvolution"; Med. Phys. 15 (4); Jul./Aug. 1988; pp. 567-575.

Carey E. Floyd, Jr., Jay A. Baker, Joseph Y. Lo, and Carl E. Ravin; "Posterior Beam-Stop Method for Scatter Fraction Measurement in Digital Radiography"; Investigative Radiology; Feb. 1992; pp. 199-123; vol. 27.

P. Abbott, A. Shearer, T.O'Doherty and W. Van Der Putten; "Image deconvolution as an aid to mammographic artefact identification I:basic techniques"; Proc SPIE, 1999, pp. 698-709; vol. 3661.

Alan H. Aydush and Carey E. Floyd Jr.,; "Improved image quality with Bayesian image processing in digital mammography"; Proc of SPIE, Feb. 2000; pp. 781-786; vol. 3979.

Dinko E. González Trotter, J. Eric Tkaczyk, John Kaufhold, Bernhard E.H. Claus, Jeffrey W. Eberhard; "Thickness-dependent Scatter Correction Algorithm for digital Mammography"; Medical Imaging 2002; pp. 469-478; Proceedings of SPIE vol. 4682.

J.H. Siewerdsen, D.J. Moseley and B. Bakhtiar, S. Richard, D.A. Jaffray; "The influence of antiscatter grids on soft-tissue detectability in cone-beam computed tomography with flat-panel detectors"; Med. Phyys. 31 (12); Dec. 2004; pp. 3506-3520.

B. Ohnesorge, T. Flohr, K. Klingenbeck-Regn; "Efficient object scatter correction algorithm for third and fourth generation CT scanners"; European Radiology 9 (3); 1999, pp. 563-569.

M. Zellerhoff, B. Scholz, E.-P. Rührnschopf and T. Brunner; "Low contrast 3D-reconstruction from C-arm data"; Proceedings of SPIE, Medical Imaging 2005; pp. 646-655; vol. 5745.

David G. Kruger, Frank Zink, Walter W. Peppler, David L. Ergun and Charles A. Mistretta; "A Regional convolution kernel algorithm for scatter correction in dual-energy images: comparison to single-kernel algorithms"; Med. Physics 21 (2), Feb. 1994; pp. 175-184.

* cited by examiner

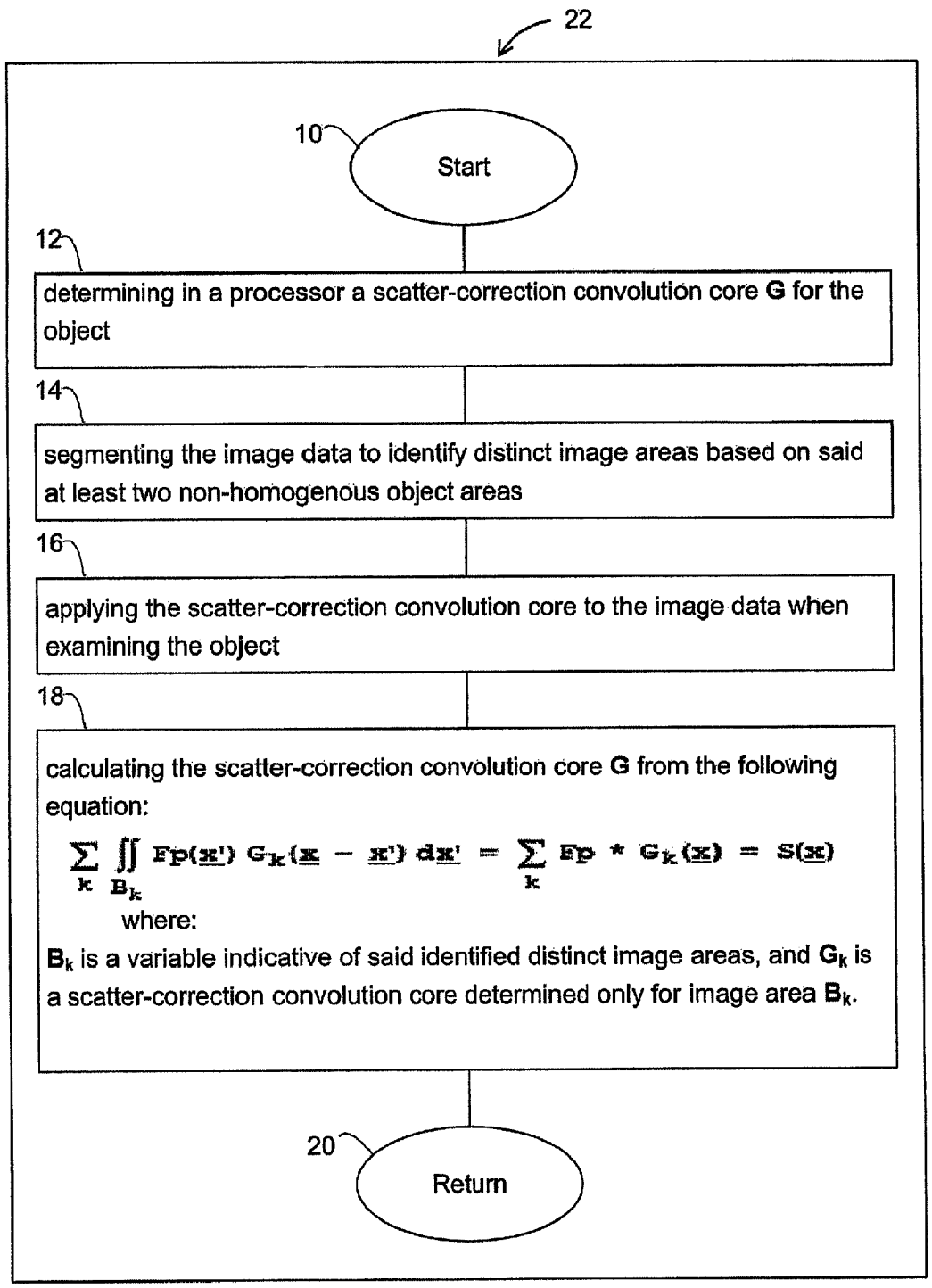

METHOD FOR CORRECTING X-RAY SCATTER IN PROJECTION RADIOGRAPHY AND COMPUTER TOMOGRAPHY

CROSS REFERENCE TO RELATED APPLICATIONS

This application claims priority of German application No. 10 2006 045 722.6 filed Sep. 27, 2006, which is incorporated by reference herein in its entirety.

FIELD OF THE INVENTION

The invention relates to a method for determination of convolution cores for correction of x-ray scatter in projection radiography and computer tomography.

BACKGROUND OF THE INVENTION

In projection radiography the x-ray scatter occurring in the patient leads to deterioration in the contrast and an increase in the noise. For quantitative applications, such as dual-energy projection imaging, e.g. in accordance with publication [Wa00], or computer tomography (CT), x-ray scatter also leads to quantitative distortions or artifacts which can adversely affect diagnosis. This problem assumes topical interest for CT with flat panel detectors (CBCT=Conebeam CT). Whereas with conventional CT systems with just a few detector rows an effective suppression of x-ray scatter can still be achieved with collimators, with CT with flat panel detectors this is no longer the case and other solutions must be found.

In projection radiography anti-scatter grids are frequently used directly above the detector input surface in order to reduce x-ray scatter. The benefit of anti-scatter grids for CBCT imaging is currently still a controversial subject in discussions but its use is to be recommended at least for a high proportion of x-ray scatter [SMB04]. As a rule however the reduction of x-ray scatter through anti-scatter grids is not sufficient so that additional computational x-ray scatter-correction processes are necessary.

With dual-energy imaging in the thorax area the patient is usually positioned very close to the detector, i.e. operation is with a very small air gap, the result of which is that, despite anti-scatter grids, the x-ray scatter intensity can overwhelm even the primary intensity, above all in the regions of the image with strong attenuation and with higher photon energies corresponding to x-ray tube voltages of >100 kV.

For around 20 years, especially since digital techniques began to spread in radiography, proposals for computational correction of x-ray scatter have been published in technical literature. Since more precise computing methods, such as Monte Carlo models for example, involve far too much effort for real-time-processing, right from the outset and to date so-called convolution computing models have been discussed. In this connection the reader is referred to the publications [LoK87], [SeB89] and [ASO99].

With the convolution cores used in literature a degree of arbitrariness obtains. Thus for example Love and Kruger in [LoK87] have investigated parametric mathematical convolution cores, i.e. rectangular, triangular, Gaussian and exponential cores. In these cases however the authors use homogeneous scatter bodies. Given these simple requirements, the differences for corresponding adaptation of the cores were not very large.

Other authors [BaF00] decide on one core type in advance, a Gaussian or exponential core is preferably used, which appears suitable. Yet other authors [TTK02] have proposed cores dependent on the tissue thickness, e.g. the thickness of the breast in mammography.

Approaches such as those stated above are primarily suitable for conditions in which largely homogeneous material is present, i.e. with relatively small differences in the thickness and the atomic composition. Mammography is a typical example of this.

With strongly inhomogeneous scatter objects, such as with bone structures and soft tissue regions—e.g. cranium, thorax, abdomen, pelvis—purely mathematical convolution cores are less suitable for describing x-ray scatter propagation and deliver unsatisfactory results.

SUMMARY OF THE INVENTION

The object of the invention is thus to find a method for determination of convolution cores for correcting the x-ray scattering in projection radiography and computer tomography which better describes the x-ray scattering actually occurring and thus compensates for it in an improved way.

This object is achieved by the features of the independent claims. Advantageous developments of the invention are the object of subordinate claims.

Basically the propagation of the x-ray scatter depends to a great extent on the scatter object, i.e. especially on the anatomy (cranium, thorax, abdomen, pelvis, etc.) and the direction of observation (e.g. lateral or anterior-posterior). In addition however dependencies on further acquisition parameters also exist: Tube voltages, spectral pre-filtering, field size, air gap, type of the x-ray scatter pattern, etc. The inventor thus proposes defining and using convolution cores adapted to specific applications, i.e. convolution cores which differ according to organ or anatomy and possibly also according to direction of observation.

Such specifically optimized convolution cores allow a better estimation of the x-ray scatter distribution which is a prerequisite for x-ray scatter correction. As regards the actual correction the reader is referred to algorithms described in literature, e.g. [ZSR05]—however the mathematical cores specified in the literature are to be replaced by the inventive cores.

BRIEF DESCRIPTION OF THE DRAWINGS

The sole FIGURE is a flow chart depicting actions or steps regarding an example method embodying aspects of the present invention.

DETAILED DESCRIPTION OF THE INVENTION

The basic idea for obtaining convolution cores adapted to specific applications is first sketched out below and this is followed by the more detailed mathematical presentation together with different exemplary embodiments.

The characteristics of x-ray scatter convolution models are as follows:

It is a physical fact that, apart from the noise, the spatial distribution of the x-ray scatter in the detector plane is rather smooth by comparison with the primary radiation, i.e. low-frequency. The basic idea of the convolution model is now to represent the distribution of the x-ray scatter as greatly-smoothed, i.e. lowpass-filtered transformation of the primary radiation distribution. More precisely however it is not the distribution of the primary radiation which is used, but a suitable "spatially-windowed" primary radiation distribution. The model approach is therefore $$H*G=S, \quad (I)$$

in this case

H is the "spatially-windowed" primary radiation distribution in the detector plane;

S is the x-ray scatter distribution; and

G is a suitable "scatter convolution core" (x-ray scatter blurring core or x-ray scatter propagation core), which is to be selected empirically so that the equation is satisfied "as well as possible".

Convolution equations of type (I) are well known in signal processing, image processing and physics. The conventional task of inversion of a convolution equation normally consists of enabling a transformed signal S to be measured that has originated by convolution with a transmission core which is required to be known G—often a blurring—from an original signal H, and that the original signal H is to be computed back or restored from equation (I).

The inventive idea consists of swapping the conventional role of H and G in the convolution equation (I), which requires both H, the "spatially windowed" primary radiation distribution, and also S, the x-ray scatter distribution, to be known and conversely for the convolution core G to be unknown and to be determined. Formally this results in the "solution" of $$G=H^{-1}*S \quad (II)$$

Because of inevitable data measurement errors and because the convolution approach (I) basically only approximately applies, there is generally no exact solution, i.e. the symbol $H^{-1}$ in (II) is only to be understood in a generalized sense. Different methods for approximative solution and optimization are described further below. Furthermore there are different embodiments of the inventive idea as regards the manner in which the data H and S are obtained.

By contrast with largely object-independent "parametric" convolution cores previously proposed in specialist literature, of which the blurring property is characterized by a mathematical parameter, object-dependent non-parametric convolution cores are proposed here which are better adapted in the sense of an optimization criterion to specific organ-dependent applications. A better estimation and correction of the x-ray scatter can be obtained in this way.

The sole FIGURE is a flow chart depicting actions or steps regarding an example method embodying aspects of the present invention. As shown in the FIGURE, subsequent to start step 10, step 12 allows determining in a processor 22 a scatter-correction convolution core G for the object. The object has at least two object areas having different scattering properties. The convolution core G is an object-dependent non-parametric convolution core. Step 14 allows segmenting the image data to identify distinct image areas based on the at least two non-homogenous object areas. Step 16 allows applying the scatter-correction convolution core to the image data when examining the object. Prior to return step 20, step 18 allows calculating the scatter-correction convolution core G from the following equation:

$$\sum_k \int\int_{B_k} F_p(\underline{x}')G_k(\underline{x}-\underline{x}')d\underline{x}' = \sum_k F_p * G_k(\underline{x}) = S(\underline{x})$$

where:

$B_k$ is a variable indicative of said identified distinct image areas, and $G_k$ is a scatter-correction convolution core determined only for image area $B_k$.

This does not make the actual correction algorithm as convolution algorithm any more complex than when parametric convolution cores are used.

The inventor typically proposes different embodiments of the manner in which the primary radiation data H and the x-ray scatter data S can be obtained for different anatomical phantoms and/or organ regions of patients.

One variant relates to measurements with the proven "beam-stop method", as described in publication [FBL92]. The advantage lies in the fact that measurements are obtained under real physical conditions. A disadvantage in this case is the experimental outlay and above all the fact that an additional data acquisition with additional exposure to radiation, even if this is to be kept small, is required, and that it is thus generally difficult to find a clinical indication with which such an additional measurement could be justified on a living patient.

In accordance with a further variant both a Monte Carlo simulation computation can be performed as well as the computation being carried out on actual patients and their digital 3-dimensional, anatomical volume representations consisting of voxels, e.g. CT reconstruction results.

Further different forms of embodiment are produced by the different mathematical methods described below for approximative inversion of the convolution equation to obtain adapted scatter convolution cores.

In the inventive basic idea described above explicit account is taken of the fact that for an x-ray scatter convolution model the scatter convolution cores G are strictly speaking dependent on the scatter object.

In concrete terms for different phantoms and/or organ regions measurements of projection data can be recorded both of the primary radiation and also of the x-ray scatter distribution, e.g. with the aid of the beam-stop method. Alternatively scatter bodies, such as phantoms or organ regions for example, can also be used in a digital way, e.g. through a 3-dimensional volume consisting of voxels, which might have been recorded and reconstructed by means of CT. From this the x-ray scatter and primary scatter distribution can be computed in the detector plane by means of Monte Carlo simulation computations. Then the convolution equations (4) or (6) below are employed respectively, to obtain the scatter convolution core G from this by inversion. The inversion will mostly not be possible exactly, i.e. the inversion is to be undertaken in the generalized sense (Moore-Penrose pseudo inversion or Fourier deconvolution with regularization) which can also be interpreted as least-squares fit.

In this way scatter convolution cores obtained "semi-empirically" can be stored as default basic forms in a library and used on an application-specific or organ-specific basis. The adaptation to the respective physical recording conditions can be undertaken by additional parameters, correction factors and/or scale changes.

The inversion method is described below:

In respect of application to flat-panel detectors $\underline{x}=(x,y)$ and $\underline{x}'=(x',y')$ indicate 2-dimensional local vectors on the detector.

In the case of a row detector $\underline{x}=x$ is the scalar position of a detector pixel. $I(\underline{x})$ is the primary intensity at the location of a detector pixel $\underline{x}$, after the x-ray beam has passed through the patient. $I_0$ is the unattenuated intensity. Primary intensity here means the direct radiation without x-ray scatter. "Normalization" is to be understood as division by $I_0$.

The basic assumption is made that the normalized x-ray scatter distribution $$S(\underline{x}) \tag{1}$$

and the normalized primary intensity distribution $$I(\underline{x})/I_0=\exp(-p(\underline{x})) \tag{2a}$$

are known from measurement or from Monte Carlo simulation.

The logarithmic projection function is then $$p(\underline{x})=-\log(I(\underline{x})/I_0). \tag{2b}$$

From equations (2a) and (2b) the "forward scatter function" can be formed, with:

$$Fp(\underline{x})=p(\underline{x})\cdot\exp(-p(\underline{x}))=-\log(I(\underline{x})/I_0)\cdot I(\underline{x})/I_0 \tag{3}$$

It is pointed out that the "forward scatter function" is the most important example of a "spatially-windowed" intensity distribution. For other examples please refer to publication [ORK96]. The spatial windowing has the sense here of forcing the unattenuated intensity outside the projection shadowing of the scattering object cross-section to zero.

The convolution equation $$\int\int Fp(\underline{x}')G(\underline{x}-\underline{x}')d\underline{x}'=Fp*G(\underline{x})=S(\underline{x}) \tag{4}$$

is now to be solved for G. Multiplicative prefactors have been omitted in this convolution equation to improve clarity.

Actually the equation (4) is to be interpreted in discretized form. Fp and S are given by measurement or "Monte Carlo" simulation. G is a sought convolution core.

Different approaches are preferably proposed for resolution of the convolution equation (4):

1. Fourier Transformation

If the spatially-windowed primary intensity distribution is written in abbreviated form as $$H=Fp, \tag{5}$$

then the convolution equation (4) can be written in a simpler form as $$H*G=S. \tag{6}$$

The convolution in equation (6) is in general not cyclic. However it can be made cyclic by "zero padding", i.e. H and S are extended at the beginning and at the end with sufficiently many zeros.

The inversion of the convolution equation (6) can then be formally attempted by discrete Fourier transformation. It is known that by Fourier transformation the convolution is transformed into the point multiplication of the Fourier transformed. The Fourier transformation is identified by the symbol ^. The following equation then applies $$H\hat{}\cdot G\hat{}=S\hat{}. \tag{7}$$

The arguments of the functions in the equation (7) are local frequencies.

In the strict sense the inversion capability is not generally ensured. This can have a number of causes. For example through inevitable inaccuracies in the measurement or "Monte Carlo" simulation of the primary radiation and x-ray scatter distribution. Also because of the fact that the convolution approach (4) only represents an approximation. Heavy fall-off of the Fourier spectrum H^ for high frequencies is a sign of the problem of inversion being "badly put". In addition zeroing can occur in H^. In such cases division by H^ is not directly possible on the right-hand side in equation (7), since the inverse Fourier spectrum of H^ can assume very large values in this case a so-called regularization can be undertaken. This corresponds to a frequency filtering of the inverse Fourier spectrum to H^. The frequency filtering is controlled by a parameter $k\sigma^2$.

If the Fourier transformation is identified by the symbol ~ an "object-adapted scatter convolution core" G is obtained $$G = G_{(k\sigma^2)} = \left(\frac{S\hat{}\overline{H\hat{}}}{(H\hat{}\overline{H\hat{}} + k\sigma^2)}\right)^{\sim}. \tag{8}$$

In this case $\sigma^2$ takes account for example of the variance of the measurement errors. The regularization can be further adapted with the factor $k\geq0$. Because of the regularization this only involves an approximative inversion of convolution equation (6), and the "scatter convolution core" G obtained still being dependent on the regularization parameter. This can however be optimized in accordance with suitable optimization criteria: For example the error functional $$\Phi(k\sigma^2)=|Fp*G_{(k\sigma^2)}-S| \tag{9}$$

can be minimized, with ∥ indicating a suitable degree of error. In the case of mean quadratic deviation a "least-squares fit" is involved. The regularization parameter $k\sigma^2$, for which the error functional (9) is minimal, is then "optimal".

2. Matrix Equation with Toeplitz Matrices

To simplify the presentation a 1-dimensional case is shown. The generalization to the 2-dimensional case is analogously mathematically transferable.

The convolution of two vectors can be formulated as a matrix operation.

The convolution of the vector H with the vector G is synonymous with the application to the vector G of the Toeplitz matrix $\underline{H}$ assigned to vector H. The following applies:

$$H*G=\underline{H}G \tag{10}$$

The Toeplitz matrix assigned to a vector H is formed as follows:

The vector H, is written in the first line or column, the next is produced by shifting the previous by an Index, and it continues successively in this way. The index shift is generally not cyclical, this approach is thus more general than the 1st approach using Fourier transformation.

The convolution equation (6) then turns into the linear equation system $$\underline{H}G=S \tag{11}$$

$\underline{H}$ is generally badly conditioned or not able to be inverted A regularized generalized inverse is $$(\underline{H}^T\underline{H}+k\sigma^2\underline{I})^{-1}\underline{H}^T \tag{12}$$

Here $\underline{I}$ means the unity matrix and $H^T$ the transposed matrix for H. For the inversion of Toeplitz matrices there are efficient algorithms with which the inverse matrix in (12) can be numerically calculated. The regularization parameter $k\sigma^2$ controls the fact that the small Eigen values of $\underline{H}^T\underline{H}$ do not come into effect during the inversion. With k=0 the Moore-Penrose pseudo-inverse would be produced.

A "semi-empirical" scatter convolution core G, is thus obtained which still depends on the selected regularization parameter, from a given scatter intensity distribution S and from a spatially-windowed primary intensity distribution H by means of $$G = G_{(k\sigma^2)} = (\underline{H}^T\underline{H} + k\sigma^2\underline{I})^{-1}\underline{H}^T S \quad (13)$$

The regularization parameters can be optimized in a similar way to equation (9) above.

3. Location-Variant Convolution Approach

A further improvement of the method can be obtained by segmenting the projection image into subareas (e.g. depending on whether soft tissue or bone dominates) and for which subareas of different specific scatter convolution cores are obtained and used.

Previously the requirement has been for the convolution model for x-ray scatter to be able to be described by a single convolution core G over the entire object cross section. This is however a simplification of the state of affairs. If for example areas of the projection image predominantly lie behind soft tissue, but other areas predominantly behind bone, then a single scatter convolution core only represents a compromise.

A more precise modeling is obtained if different convolution cores are used in different image areas, e.g. depending on whether the presence of soft tissue or bone predominates. The subdivision into different areas is obtained by segmentation of the projection image. The generation of a specific scatter convolution core in each area is undertaken by application of the methods described above to the corresponding image in each case. The convolution equation (4) is then inventively replaced by a total and the following applies:

$$\sum_k \int_{B_k} \int Fp(x') G_k(x - x') dx' = \sum_k Fp * G_k(x) = S(x) \quad (14)$$

In equation (14) $B_k$ means the image areas separated out by segmentation, $G_k$ is the respective scatter convolution core belonging only to area $B_k$.

In accordance with the ideas set out above, the inventor proposes a method for correction of x-ray scatter in projection radiography or x-ray computer tomography, with different scatter-correction convolution cores G being determined for differently observed objects and in the investigation of the respective objects object-specific scatter-correction convolution cores being applied to detector data which are created when these objects are x-rayed.

In a particular embodiment at least one object-specific scatter-correction convolution core G can be computed from the equation $G = H^{-1}*S$, with H representing the "spatially-windowed" primary radiation distribution in the detector plane and S representing the x-ray scatter distribution.

Furthermore it is proposed that the scatter-correction convolution cores be defined on the basis of practical phantom investigations.

Preferably however the scatter-correction convolution cores can also be defined on the basis of theoretical phantom investigations, especially on the basis of "Monte Carlo" computations.

In the specific case of the examination of a patient it is further proposed, depending on the organ or depending on the anatomy being examined, to use different scatter-correction convolution cores for the x-ray scatter correction.

In addition it is also possible in accordance with a further improved variant for the object under examination, preferably a patient, to be segmented into areas of different x-ray scatter production to be expected and for different scatter-correction convolution cores to be used for x-ray scatter correction for each observed area.

For a further refinement of the inventive method different scatter-correction convolution cores can also be determined and used for each direction of x-raying relative to the object examined.

Inventively an improvement of the method is also proposed, with:

a reconstruction of the volume data of the object being initially performed either without or with insufficient x-ray scatter correction, on the basis of this volume data at least one convolution volume core being determined, subsequently an x-ray scatter correction being applied to the originally determined detector data by the at least one new scatter-correction convolution core determined, and a reconstruction being undertaken with the new corrected detector data without new measurement.

The scatter-correction convolution cores are thus determined and stored in advance. For the actual scan of the patient the corresponding correction core as a function of the corresponding application is then retrieved in "real time", e.g. the scan of a specific organ or a specific body region. Where necessary this can still be adaptively modified before use.

It is also useful if, for the computation of the scatter-correction convolution core G the equation $$G = G_{(k\sigma^2)} = \left(\frac{S^\wedge \overline{H^\wedge}}{(H^\wedge \overline{H^\wedge} + k\sigma^2)}\right)^\sim$$

is used, with the symbol ~ identifying the Fourier back transformation, $\sigma^2$ the variance of the measurement error and $k \geq 0$ a factor for regularization.

Alternatively, for the computation of the scatter-correction convolution core G the equation $$G = G_{(k\sigma^2)} = (\underline{H}^T\underline{H} + k\sigma^2\underline{I})^{-1}\underline{H}^T S$$

can also be used with $\underline{I}$ identifying the unity matrix and $\underline{H}^T\underline{H}$ the small Eigen values and $k\sigma^2$ representing a regularization parameter such that with the matrix inversion the small Eigen values of the matrix $\underline{H}^T\underline{H}$ do not have a disruptive effect. The formation of the Toeplitz matrix is defined after eq. (10) and with the aid of eq. (5).

The two last-mentioned variants can be minimized for optimizing the scatter-correction convolution core of the error functional $\Phi(k\sigma^2) = |Fp*G_{(k\sigma^2)} - S|$, with || being a suitable measure of error e.g. the error square norm, which is calculated as the generally weighted total of the squared differences summed over all pixels. With pixel-dependent weighting factors it is still possible to influence in this case how strongly the individual pixels are rated, e.g. depending on their position, e.g. on the edge of the measurement field, or depending on the local primary intensity in the error square sum.

An improvement of the inventive basic method is also achieved if, for computation of the scatter-correction convolution core G, the equation $$\sum_k \int_{B_k} \int Fp(\underline{x}')G_k(\underline{x}-\underline{x}')d\underline{x}' = \sum_k Fp*G_k(\underline{x}) = S(\underline{x})$$

is used, with $B_k$ identifying the image areas separated by segmentation, $G_k$ the scatter-correction convolution core only belonging to the area $B_k$ in each case.

Naturally the features of the invention given in this document cannot only be used in the combination specified but also in other combinations or on their own, without departing from the framework of the invention.

The invention claimed is:

1. A method for correcting an x-ray scatter in an image data of an object, comprising:
    determining in a processor a scatter-correction convolution core G for the object, wherein the object has at least two object areas having different scattering properties, wherein the convolution core G is an object-dependent non-parametric convolution core;
    segmenting the image data to identify distinct image areas based on said at least two object areas; and
    applying the scatter-correction convolution core to the image data when examining the object, wherein the scatter-correction convolution core G is calculated from an equation defined as follows:

$$\sum_k \int_{B_k} \int Fp(\underline{x}')G_k(\underline{x}-\underline{x}')d\underline{x}' = \sum_k Fp*G_k(\underline{x}) = S(\underline{x})$$

wherein:
   $B_k$ is a variable indicative of said identified distinct image areas,
   $G_k$ is a scatter-correction convolution core determined only for image area $B_k$.

2. The method as claimed in claim 1, wherein the scatter-correction convolution core G is calculated from an equation $G=H^{-1}*S$,
    wherein:
       H represents a "spatially-windowed" primary radiation distribution in a detector plane, and
       S represents an x-ray scatter distribution.

3. The method as claimed in claim 1, wherein the scatter-correction convolution core is determined based on practical phantom examination.

4. The method as claimed in claim 1, wherein the scatter-correction convolution cores is determined based on theoretical phantom examination.

5. The method as claimed in claim 4, wherein the theoretical phantom examination is Monte Carlo computation.

6. The method as claimed in claim 1, wherein the object is a patient and a plurality of different scatter-correction convolution cores are determined depending on an organ of the patient to be examined.

7. The method as claimed in claim 1, wherein the object is a patient and a plurality of different scatter-correction convolution cores are determined depending on an anatomy of the patient to be examined.

8. The method as claimed in claim 1, wherein the object is segmented into a plurality of areas of different x-ray scatter production and a plurality of different scatter-correction convolution cores are determined for each area.

9. The method as claimed in claim 1, wherein the scatter-correction convolution core is further determined based on a direction of an x-ray beam for imaging the object.

10. The method as claimed in claim 1,
    wherein a volume data of the object is initially reconstructed from the image data either without or with an insufficient x-ray scatter correction,
    wherein at least one scatter-correction convolution core is determined to the volume data,
    wherein an x-ray scatter correction is subsequently applied to the image data by the at least one determined scatter-correction convolution core, and
    wherein the volume data is reconstructed again from the corrected image data without a new measurement.

11. The method as claimed in claim 1, wherein the scatter-correction convolution core G is calculated from an equation $$G = G_{(k\sigma^2)} = \left( \frac{S^\wedge \overline{H^\wedge}}{(H^\wedge \overline{H^\wedge} + k\sigma^2)} \right)^\sim$$

wherein:
   $\sim$ identifies a Fourier back transformation,
   $\sigma^2$ identifies a variance of a measurement error, and
   k identifies a factor for regularization with $k \geq 0$.

12. The method as claimed in claim 11, wherein an error function $\Phi(k\sigma^2)=|Fp*G_{(k\sigma^2)}-S|$ is minimized for optimizing the scatter-correction convolution core,
    wherein $\|$ indicates a measure of error.

13. The method as claimed in claim 1, wherein the scatter-correction convolution core G is calculated from an equation $$G=G_{(k\sigma^2)}=(\underline{H}^T\underline{H}+k\sigma^2\underline{I})^{-1}\underline{H}^TS$$

wherein:
   $\underline{I}$ indicates a unity matrix,
   $k\sigma^2$ indicates a regularization parameter, and
   $\underline{H}^T\underline{H}$ indicates a small Eigen value.

14. The method as claimed in claim 13, wherein an error function $\Phi(k\sigma^2)=|Fp*G_{(k\sigma^2)}-S|$ is minimized for optimizing the scatter-correction convolution core,
    wherein $\|$ indicates a measure of error.

15. A medical apparatus for recording an image data of an object and correcting an x-ray scatter in the image data, comprising:
    an x-ray source that emits x-rays to the object;
    an x-ray detector that records the image data by detecting the x-rays penetrated the object; and
    a control and processing unit that:
    calculates a scatter-correction convolution core G for the object, wherein the object has at least two object areas having different scattering properties, wherein the convolution core G is an object-dependent non-parametric convolution core;
    segments the image data to identify distinct image areas based on said at least two object areas; and
    applies the scatter-correction convolution core to the image data when examining the object, wherein the scatter-correction convolution core G is calculated from an equation defined as follows:

$$\sum_k \int_{B_k} \int Fp(\underline{x}')G_k(\underline{x}-\underline{x}')d\underline{x}' = \sum_k Fp * G_k(\underline{x}) = S(\underline{x})$$

wherein:
- $B_k$ is a variable indicative of said identified distinct image areas,
- $G_k$ is a scatter-correction convolution core determined only for image area $B_k$.

16. The medical apparatus as claimed in claim 15, wherein the scatter-correction convolution core G is calculated from an equation $G=H^{-1}*S$, wherein:
- H represents a "spatially-windowed" primary radiation distribution in a detector plane, and
- S represents an x-ray scatter distribution.

17. The medical apparatus as claimed in claim 15, wherein the scatter-correction convolution core G is calculated from an equation $$G = G_{(k\sigma^2)} = \left( \frac{S^{\wedge}\overline{H^{\wedge}}}{\left(H^{\wedge}\overline{H^{\wedge}} + k\sigma^2\right)} \right)^{\sim}$$

wherein:
- $\sim$ identifies a Fourier back transformation,
- $\sigma^2$ identifies a variance of a measurement error, and
- k identifies a factor for regularization with $k \geq 0$.

18. The medical apparatus as claimed in claim 15, wherein the scatter-correction convolution core G is calculated from an equation $$G = G_{(k\sigma^2)} = (\underline{H}^T\underline{H} + k\sigma^2\underline{I})^{-1}\underline{H}^T S$$

wherein:
- $\underline{I}$ indicates a unity matrix,
- $k\sigma^2$ indicates a regularization parameter, and
- $\underline{H}^T\underline{H}$ indicates a small Eigen value.

\* \* \* \* \*